(12) United States Patent
Lusenti et al.

(10) Patent No.: US 10,413,526 B2
(45) Date of Patent: Sep. 17, 2019

(54) COMPOSITION FOR THE TREATMENT OF NEUROPATHIES AND/OR NEUROPATHIC PAIN

(71) Applicant: Kolinpharma S.p.A., Milan (IT)

(72) Inventors: Emanuele Lusenti, Milan (IT); Ritapaola Petrelli, Milan (IT)

(73) Assignee: Kolinpharma S.p.A., Milan (IT)

( * ) Notice: Subject to any disclaimer, the term of this patent is extended or adjusted under 35 U.S.C. 154(b) by 160 days.

(21) Appl. No.: 15/562,991

(22) PCT Filed: Mar. 25, 2016

(86) PCT No.: PCT/IB2016/051709
§ 371 (c)(1),
(2) Date: Sep. 29, 2017

(87) PCT Pub. No.: WO2016/157053
PCT Pub. Date: Oct. 6, 2016

(65) Prior Publication Data
US 2018/0055820 A1 Mar. 1, 2018

(30) Foreign Application Priority Data

Mar. 31, 2015 (IT) .......... 102015000010454

(51) Int. Cl.
| | |
|---|---|
| *A61K 9/20* | (2006.01) |
| *A61K 9/50* | (2006.01) |
| *A61K 31/12* | (2006.01) |
| *A61K 31/51* | (2006.01) |
| *A61K 31/221* | (2006.01) |
| *A61K 31/355* | (2006.01) |
| *A61K 31/375* | (2006.01) |
| *A61K 31/385* | (2006.01) |
| *A61K 31/525* | (2006.01) |
| *A61K 31/675* | (2006.01) |
| *A61K 31/714* | (2006.01) |

(52) U.S. Cl.
CPC .......... *A61K 31/385* (2013.01); *A61K 9/2054* (2013.01); *A61K 9/2077* (2013.01); *A61K 9/501* (2013.01); *A61K 9/5047* (2013.01); *A61K 31/12* (2013.01); *A61K 31/221* (2013.01); *A61K 31/355* (2013.01); *A61K 31/375* (2013.01); *A61K 31/51* (2013.01); *A61K 31/525* (2013.01); *A61K 31/675* (2013.01); *A61K 31/714* (2013.01)

(58) Field of Classification Search
CPC .............. A61K 2300/00; A61K 31/221; A61K 9/2077; A61K 31/12
See application file for complete search history.

(56) References Cited

U.S. PATENT DOCUMENTS

2006/0051418 A1* 3/2006 Cowen ................ A61K 9/0004
424/468

FOREIGN PATENT DOCUMENTS

| | | |
|---|---|---|
| EP | 0256999 A2 | 2/1988 |
| WO | 00/11968 A1 | 3/2000 |
| WO | 2004047717 A2 | 6/2004 |
| WO | 2010/115947 A2 | 10/2010 |
| WO | 2016/027224 A1 | 2/2016 |

OTHER PUBLICATIONS

Han et al., "A systematic review and meta-analysis of α-lipoic acid in the treatment of diabetic peripheral neuropathy", European Journal of Endocrinology, 2012, vol. 167, pp. 465-471.
Mannelli et al., "The Neuropathy-Protective Agent acetyl-L-carnitine Activates protein kinase C-γ and MAPKs in a Rat Model of Neuropathic Pain", Neuroscience, 2010, vol. 165, pp. 1345-1352.
Zanjani et al., "The Attenuation of Pain Behavior and Serum SOC-2 Concentration by Curcumin in a Rat Model of Neuropathic Pain", The Korean Journal of Pain, 2014, vol. 27, No. 3, pp. 246-252.
PCT International Search Report and the Written Opinion, Application No. PCT/IB2016/051709 filed Mar. 25, 2016, dated Jul. 8, 2016.
PCT International Preliminary Report on Patentability, Application No. PCT/IB2016/051709 filed Mar. 25, 2016, dated Jul. 11, 2017.

* cited by examiner

*Primary Examiner* — Kortney L. Klinkel
(74) *Attorney, Agent, or Firm* — MacMillan, Sobanski & Todd, LLC

(57) ABSTRACT

A pharmaceutical composition or dietary supplement effective in the treatment of neuropathies and/or neuropathic pain is described, which comprises, as the active ingredients, the combination of curcumin, N-acetyl-L-carnitine and alpha-lipoic acid, wherein N-acetyl-L-carnitine and alpha-lipoic acid are present in the composition in the form of coated particles.

7 Claims, No Drawings

COMPOSITION FOR THE TREATMENT OF NEUROPATHIES AND/OR NEUROPATHIC PAIN

This is a national stage application filed under 35 U.S.C. § 371 of international application PCT/IB2016/051709, filed under the authority of the Patent Cooperation Treaty on Mar. 25, 2016, published; which claims the benefit of ITALY - No. 102015000010454 filed on Mar. 31, 2015. The entire disclosures of all the aforementioned applications are expressly incorporated herein by reference for all purposes.

The invention relates to a composition to be used in the field of the treatment of neuropathies and neuropathic pain.

In particular, the invention relates to a mixture of compounds capable of carrying out both a neuroprotective action, mediated by anti-inflammatory and antioxidant activities, and a neurotrophic and energising action capable of providing nourishment to the fibres and, through an increase in the energy metabolism, of restoring the damaged neuronal cell membranes and therefore normal nerve conduction.

The object of the invention is a formulation that can be administered orally, free from particular contraindications both in relation to the subjects to which it can be administered and the amounts administered, having anti-inflammatory, antioxidant and neurotrophic effects and therefore effective in the treatment of neuropathies and neuropathic pain.

Neuropathy is a disorder that affects the peripheral nervous system with the exception of the I and II cranial nerves, i.e. the olfactory nerve and the optic nerve, respectively. The neuropathy may be localized in a single nerve (mononeuropathy) or in several nerves (polyneuropathy).

There are different types of degeneration which affect the nerve fibre:

(i) Wallerian degeneration following axon or nerve interruption with maintenance of connective tissue: axon swelling together with myelin destruction and phagocytosis of globular lipid formations appear after approximately 48 hours; after a few days, budding is detected, which can be ascribed to attempts at regeneration, with recovery of about 1 mm per day.

(ii) Axonal degeneration as a result of metabolic changes: initially it affects the distal parts of the fibre with slow progression in the proximal direction.

(iii) Segmental demyelination due to primitive damage to the Schwann cells caused by metabolic changes, inflammatory processes, and toxic damage: a progressive slowing of the pulse is observed, up to blockage when demyelination affects a fibre length greater than 3 internodes, axonal distress and attempts at remyelination by new proliferating cells is seen, but the succession of demyelination and remyelination processes causes a thickening of the nerve fibre through interposition of fibroblasts and collagen, with formation of palpable onion bulb-like fibres on the skin (Dejerine-Sottas hypertrophic, amyloidotic, and chronic demyelinating inflammatory polyneuropathies).

On the basis of the aetiology, neuropathies can be classified as follows:
demyelinating inflammatory neuropathies (e.g. Guillain-Barré-syndrome);
neuropathies due to infectious agents (for example, HIV, Epstein-Barr, leprosy, sarcoidosis);
metabolic neuropathies (diabetes, porphyrias, hypothyroidism);
toxic-nutritional neuropathies (alcohol, hypovitaminosis, drugs, toxic metals);
paraneoplastic neuropathies;
paraproteinemic neuropathies (amyloidosis, gammopathies, cryoglobulinaemias);
neuropathies in the course of connective tissue diseases;
hereditary neuropathies (e.g. Charcot-Marie-Tooth syndrome).

Peripheral neuropathies are therefore a heterogeneous group of disorders of the peripheral nerves. The causes are manifold and, as mentioned above, are represented by hereditary and metabolic factors, oxidative stress on the nervous tissue, trauma, infection and inflammation. The majority of peripheral neuropathies features symptoms such as pain, muscle weakness and sensory loss, which result in an overall physical disability of the patients.

Neuropathic pain is pathological as it serves no useful or protective function for the organism; in fact, it is characterized by a process of amplifying nociceptive messages, which can occur both in the peripheral and central nervous systems.

Unlike somatic pain, which originates from specialised nerve endings (pain sensors on the skin) and is felt through tissue damaging, neuropathic pain arises directly from nerve dysfunction and does not imply ongoing damage.

Neuropathic pain is a common symptom in peripheral neuropathies dependent on the length of the nerve and, often, it is the first symptom thereof. Therefore, peripheral neuropathy can be defined as a pathological process that mainly affects the small-diameter myelin fibres or the unmyelinated fibres.

Neuropathic pain is associated with numerous types of sensory signs and symptoms that may occur alone or together with other specific manifestations in patients with neuropathic pain.

Among the various hypothesized and demonstrated aetiopathogenetic mechanisms underlying the signs and symptoms of mechanical peripheral neuropathies, alteration of sodium channels (diabetic neuropathies), neuronal hyperexcitability, sudden changes in spinal connectivity, and strong oxidative stress on the nervous tissue can be mentioned. The mediators of inflammatory processes also appear to have a specific role in the onset of degenerative and inflammatory neuropathies.

In summary, the causes of painful symptoms in the upper and lower limbs are many and of various origin, and may be related to the orthopaedic field (myalgias, compressive or traumatic neuropathies). In fact, a significant percentage of these pain syndromes of the limbs is due to irritative or compressive radiculopathies, with cervical relevance in the case of the upper limbs, and lumbo-sacral with respect to the lower limbs, the most common cause of which is represented by a herniated disc.

The composition object of the present invention, effective in the treatment of neuropathies and neuropathic pain, comprises the combination of curcumin, N-acetyl-L-carnitine and alpha-lipoic acid as the active ingredients, and is characterized in that it comprises a polyvalent matrix in the form of an agglomerate formed by N-acetyl-L carnitine particles and alpha-lipoic acid particles or N-acetyl-L-carnitine particles in admixture with alpha-lipoic acid, said particles being directly coated with one or more layers of coating membrane capable of isolating the relevant active ingredient from the external environment and of regulating the release thereof in a predetermined manner, the coating membrane consisting of talc, silicon dioxide and ethylcellulose.

Compared to the state of the art, the solution illustrated above, which forms the object of the present invention, advantageously allows to eliminate the need to use an inert support core for the active ingredients, as instead contemplated for conventional pharmaceutical formulations, allowing at the same time to achieve titres of the active ingredients which are distinctly higher than those of conventional microgranules, pellets and minipellets.

Moreover, the coating has a threefold advantage: the masking of the flavour, the control of the release and a productive advantage. The latter refers to the potential of producing tablets including both N-acetyl-L-carnitine and alpha-lipoic acid, avoiding the reaction between the two substances.

In a preferred embodiment, the active ingredients N-acetyl-L-carnitine and alpha-lipoic acid contained in the composition of the present invention are in the form of particles having a particle size comprised between 200 and 700 μm.

Additional features of the composition of the invention and the use thereof are defined in the appended claims, which form an integral part of the present description.

Curcumin, IUPAC name (1E,6E)-1,7-bis-(4-hydroxy-3-methoxyphenyl)-hepta-1,6-dien-3,5-dione, is a compound belonging to the class of polyphenolic compounds. It is obtained by solvent extraction from the dried and ground rhizome of the *Curcuma longa* plant.

*Curcuma longa* is a plant native of South East Asia and is traditionally used as a spice. This plant is known from ancient times for its high antioxidant properties and is traditionally used for treatment of inflammation, gastrointestinal, liver and other disorders. Its ability to counteract the action of free radicals is far greater than that of the other known natural antioxidants. *Curcuma* is indeed rich in active ingredients, in particular curcuminoids and among these more particularly curcumin. Thanks to its antioxidant and anti-inflammatory activity, *Curcuma longa* is considered as a cell bioprotector, capable of actively contributing to restoration of the basal conditions of the compromised neuronal environment.

In contrast to other antioxidants, curcuminoids are capable both of preventing the formation of free radicals and of enhancing the activity of alpha-lipoic acid, neutralising the radicals already present at the tissue level.

As regards the anti-inflammatory activity, there are many studies that confirm the action of *curcuma* at different levels, allowing it to be regarded as a very powerful inhibitor of the inflammatory cascade: at the gene level, it inhibits the expression of cyclooxygenase-2, it inhibits the activity of lipoxygenase-5 and the production of prostaglandins by cyclooxygenases 1 and 2. It also inhibits the activation of proinflammatory cytokines (TNF-α, IL-1β), adhesion molecules, growth factor receptors and vascular endothelial growth factor (VEGF), activities related to tumour onset.

In the formulations according to the invention, the *Curcuma longa* extract is the preferred source of curcumin. More preferably, a *Curcuma longa* extract that has a curcumin titre of 95% is used. The *Curcuma longa* extracts also comprise some curcumin derivatives, generally known as curcuminoids, among which demethoxycurcumin and bis-demethoxycurcumin are particularly mentioned.

Alpha lipoic acid (ALA) is a very small molecule naturally occurring in two forms, the oxidized (cyclic disulfide) and the reduced (dihydrolipoic acid, with two sulphydryl groups at positions 6 and 8) forms. The two forms can be quickly interchanged and, at the level of the damaged tissue, they behave as neuroprotection and neurotrophic factors and, at the systemic level, as euglycaemic agents (an essential activity as most diabetic patients are affected by neuropathies).

The neuroprotective action is possible thanks to the antioxidant activity: it is in fact able to reduce the oxidative stress at the level of the damaged nervous tissue. The presence of free radicals results in a deterioration of the cell membranes and in particular of the Schwann cells, reducing the nerve function and the transmission performance, as well as activating the NF-kB-linked transduction pathways in a non-physiological way, which stimulates the immune response (inducing inflammation), regulates cell proliferation, the apoptosis cascade, but is also involved in the onset of cancer and autoimmune diseases. Alpha-lipoic acid is particularly effective in the neutralization of free radicals: in fact, it acts as a scavenger, but is also able to restore other powerful antioxidants at the cellular level, such as vitamin E, vitamin C, coenzyme Q and reduced glutathione.

Alpha-lipoic acid is also able to inhibit phagocytic chemotaxis at the neuronal damage and this confirms the fact that the composition according to the invention, comprising alpha-lipoic acid, is able to reduce inflammation and inhibit the damage. In fact, in the case of degeneration of the nerve fibres, the macrophages rush to the site concerned and phagocytize the surrounding myelin, amplifying the damage and further reducing the conductive capacity of the neurones involved, as well as amplifying the response by the inflammatory cascade.

Alpha-lipoic acid also exerts a neurotrophic action at two levels: increasing the energy metabolism and inducing the production of NGF (Nerve Growth Factor). The energy metabolism is sustained by the presence of alpha-lipoic acid since, already physiologically, it is a cofactor of two key enzyme complexes involved in the Krebs cycle. The first complex is pyruvate dehydrogenase, which catalyses the oxidative decarboxylation of pyruvate into acetyl-CoA, whereas the second is α-ketoglutarate dehydrogenase, which catalyses the conversion of α-ketoglutarate into succinyl-CoA, in this case, too, through oxidative decarboxylation. The two enzyme complexes are similar and the decarboxylation reactions occur with production of a high-energy thioester linkage with coenzyme A, which is possible thanks to the availability of ALA sulphydryl groups. The Krebs cycle is a metabolic cycle of fundamental importance in all cells, it allows for the formation of chemical energy (ATP) by degradation of carbohydrates, fats and proteins, but it also supplies many precursors for the production of amino acids and other essential molecules in the cell. At the nerve tissue level it is crucial to supply energy both for the maintenance of the basal cell functions, and for the restoration of membranes damaged by inflammation and oxidative stress, and for the production of neurotransmitters and vesicles that are essential for cell-cell communication, i.e. for nerve conduction that is disrupted in the case of neuropathies.

In addition to enhancing the energy metabolism, alpha-lipoic acid is able to improve the production of NGF. NGF is a signal protein involved in the development and maintenance of the nervous system. This factor promotes and directs axonal growth and, through cell signalling mechanisms, is an indispensable product during regeneration, as a growth factor.

It is known that the majority of individuals suffering from diabetes are subject to complications related to neuropathic pain. This is a further reason why alpha-lipoic acid, which has euglycemic activity, i.e. is able to intervene in the carbohydrate metabolism by resensitizing insulin receptors and restoring the physiological activity of insulin itself, was added in the composition according to the invention, assisting in drug treatment.

The third component of the composition according to the invention is N-acetyl-L-carnitine, i.e. the acetyl ester of L-carnitine, a compound physiologically occurring in all mammals. The compound is metabolized to carnitine in the blood, thanks to plasma esterases. The main function of carnitine is the transport of long-chain fatty acids from the cytoplasm to the mitochondrial matrix, subsequent to their activation into acyl-CoA. Once in the matrix, the fatty acids are used and oxidized. The function of carnitine is linked to intracellular regulation of a correct ratio between acyl-CoA and acyl carnitine, through transfer of short-chain acyl groups from the inside of the mitochondrion to the cytoplasm. The availability of L-carnitine and its esters such as N-acetyl-L-carnitine prevents accumulation of fatty acids and acyl-CoA, in the cytoplasm and the mitochondrion, respectively, and allows for establishment of acetyl-CoA at the mitochondrial site for the production of energy through the beta-oxidation cycle. The excess of acetyl-CoA would cause an increase in the number of carbohydrates that can be used for energy purposes at the expense of fatty acids. It is therefore interesting to point out that, in diabetic subjects, intake of N-acetyl-L-carnitine can improve the glucose metabolism.

The presence of N-acetyl-L-carnitine in the composition according to the invention is particularly advantageous because this substance acts on several fronts in synergy with alpha-lipoic acid. N-acetyl-L-carnitine has neurotrophic activity, being able to increase NGF production level and induce an increase in the sensitivity of the neuronal receptors to the NGF growth factor, amplifying its responses. This aspect is important for inducing the production of the myelin sheath required to maintain nerve health and function, as well as for restoring its physiological condition in case of damage.

Together with alpha lipoic acid, with which it exerts a synergistic effect, N-acetyl-L-carnitine is capable of enhancing neuronal protection by regulating, at the gene level, pathways involved in cell growth (critical for the induction of sprouting and for synaptogenesis), in the activation of anti-apoptotic proteins (to counteract the apoptotic cascade induced by NF-kB in the case of strong oxidative stress and/or damage at the nerve fibre level) and antioxidant proteins (to neutralize the environment surrounding the damaged neurons and/or prevent the oxidative damage).

The combination of the above mentioned active ingredients in the composition according to the invention is particularly advantageous as they have a synergistic effect, both with regard to the neuroprotective activity and the neurotrophic activity.

According to a preferred aspect of the present invention, the subject compositions may contain additional components with a therapeutic, or supplementary, action or otherwise useful for the purposes of the invention. Examples of said additional components are vitamin C, vitamin E, vitamin B1, vitamin B2, vitamin B6 and vitamin B12.

Vitamin B1, or thiamine, is a water-soluble vitamin that, once in the tissues, is phosphorylated to thiamine diphosphate (or pyrophosphate), its active form. Thiamine pyrophosphate (PP) is the coenzyme of keto acid and transketolase decarboxylases. In fact, it plays an important role in the oxidative decarboxylation of pyruvate and α-ketoglutarate (synergy with ALA) in the Krebs cycle and in the transketolase reaction in the pentose phosphate cycle.

Vitamin B2, or Riboflavin, is a heterocyclic compound obtained from a flavin molecule that is bound to a chain formed from ribitol. Riboflavin, once metabolised, is transformed into flavin mononucleotide (FMN) and flavin adenine dinucleotide (FAD), two coenzyme forms essential for flavin enzymes in which they act as prosthetic groups. They take part in several redox reactions in the metabolism of carbohydrates, proteins and lipids, including pyruvate oxidative decarboxylation, oxidation of fatty acids and amino acids, transport of electrons during oxidative phosphorylation.

Vitamin B6, in its three forms, pyridoxine, pyridoxal and pyridoxamine, participates in the neuroprotection mechanisms, and it also promotes conversion of tryptophan into serotonin, allowing for a reduction of the pain symptoms.

Vitamin B12, or Cobalamin, participates in the repair processes of the myelin sheath as it participates in the synthesis of phospholipids, catecholamines and phosphatidylcholine (membrane structural elements).

Vitamin E, or Tocopherol, is a liposoluble vitamin regarded as the antioxidant vitamin par excellence. In the composition according to the invention it has the purpose of increasing lipid production at the neuronal membranes, the first targets of free radicals.

Vitamin C, or ascorbic acid, is also fundamental for its known antioxidant properties. This function occurs when vitamin C oxidises and then regenerates the oxidized substances, such as iron or copper, restoring their original form. In the course of this process, the harmful oxidizing agent is removed. It is capable of blocking reactive oxygen species (ROS, such as superoxide, peroxyl and hydroperoxyl radicals), but also nitrogen ones (RNS, such as nitroxide radicals, peroxynitrites and nitrogen dioxide) which may form at the site of inflammation. Vitamin C is an essential element for the proper functioning of the brain and nervous system, in fact, it is consumed more quickly under stressful conditions.

The compositions of the invention can be formulated into any of the forms suitable for oral administration, such as for example hard or soft gelatin capsules, tablets, effervescent or chewable tablets, sachets of granules or powders, controlled release solid forms, chewing gums and the like.

The compositions of the present invention can be formulated in a way that is suitable for oral administration and will be prepared according to conventional methods well known in the pharmaceutical art, such as those described in "*Remington's Pharmaceutical Handbook*", Mack Publishing Co., N.Y., USA, using excipients, diluents, fillers, anti-caking agents acceptable for their end use.

A particularly preferred formulation of the composition of the invention is set forth hereunder.

FORMULATION EXAMPLE—1.08 G TABLET

| | |
|---|---|
| N-acetyl-L-carnitine | 400 mg |
| Alpha-lipoic acid | 300 mg |
| *Curcuma longa* dry extract | 150 mg |
| of which curcumin | 142.95 mg |
| Vitamin C | 125 mg |
| Vitamin E | 9 mg |
| Vitamin B1 (thiamine) | 6.25 mg |
| Vitamin B2 (riboflavin) | 6.25 mg |
| Vitamin B6 (pyridoxine) | 2.38 mg |
| Vitamin B12 (cyanocobalamin) | 6.25 mg |

The recommended dose is one or two tablets per day.

In the composition of the present invention, N-acetyl-L-carnitine and alpha-lipoic acid are in the form of coated particles as described above. In particular:

N-acetyl-L-carnitine: in the form of white granules. Active ingredient: N-acetyl-L-carnitine; Coating membrane: talc (anti-caking agent), colloidal silicon dioxide (opacifier) and ethylcellulose (emulsifier).

Alpha-lipoic acid: particles, yellow-coloured. Active ingredient: Alpha-lipoic acid; Coating membrane: talc (anti-caking agent), colloidal silicon dioxide (opacifier) ethylcellulose (emulsifier).

The aforesaid coating membranes are manufactured from an alcoholic solution of talc, silicon dioxide and ethylcellulose, which upon drying forms the coating of the granules of the active ingredient.

An in vitro dissolution test was performed with the above alpha-lipoic acid coated particles, which gave the following results:
- after 1 hour: 19.2%
- after 2 hours: 49.1%
- after 4 hours: 71%
- after 8 hours: 94.7%

EXAMPLE 2

To facilitate the compression process of the mixture, N-acetyl-L-carnitine hydrochloride was made more suited to compressibility through dry granulation, being a very poorly flowable and low-density component.

This process improves the following properties:
It increases the raw material's density
It favours the compressibility
It improves the flowability both of the raw material and of the whole mixture that it contacts.

Despite these precautions, the final mixture was compressed with several difficulties, reporting the following observations:

Moderate weight variability: this parameter shows that the mixture is poorly flowable and thus it fills the matrix unevenly, with the result of obtaining tablets that are uneven in terms of weight. During the entire compression process, the operator had to stop the machine and set it to ensure weights in the required range: 1050±2%

Variability of the tablet thickness: the difficulty of maintaining a constant weight also results in a consequent variability of the thickness of the tablet.

Variability of the hardness: this parameter too is variable for the reasons mentioned earlier. Hardness range recorded: 4.5-6 kg Because of these observations detected during the compression phase, also confirmed in the coating phase (if the starting core does not have constant characteristics in technological terms, the final coating phase is slower in order to ensure a low processing rate that otherwise could lead to a rupture or abrasion of the surfaces), it was decided to use N-acetyl-L-carnitine coated as described in the present patent application (coating membrane consisting of talc, silicon dioxide and ethylcellulose). The same was carried out with lipoic acid, also present in high percentage by weight in the composition of the present invention. In this way, a final mixture was obtained which was more suitable for compression, the above technological properties being improved.

During the compression process, an improvement of the technological parameters was detected:

The weight variability was reduced and the 1050±2% range was fulfilled more easily, without having to interrupt the process for setting up the machine.

The hardness is improved, allowing to obtain a hardness range of between 7-10 kg.

To further improve the technological properties of the mixture, an adjuvant, such as hydroxypropylcellulose, was added.

The invention claimed is:

1. A pharmaceutical composition or dietary supplement for use in the treatment of neuropathies and/or neuropathic pain, comprising the combination of curcumin, the acetyl ester of L-carnitine and alpha-lipoic acid as the active ingredients, characterized in that the active ingredients acetyl ester of L-carnitine and alpha-lipoic acid are present in the composition in the form of particles of acetyl ester of L-carnitine and alpha-lipoic acid, respectively, or in the form of particles of acetyl ester of L-carnitine in admixture with alpha-lipoic acid, said particles being directly coated with one or more layers of coating membrane capable of isolating the relevant active ingredient from the external environment and of adjusting the release thereof in a predetermined manner, said coating membrane consisting of talc, silicon dioxide and ethylcellulose.

2. The pharmaceutical composition or dietary supplement according to claim 1, wherein said particles of acetyl ester of L-carnitine and alpha-lipoic acid, respectively, or of acetyl ester of L-carnitine in admixture with alpha-lipoic acid, have a particle size between 200 and 700µm.

3. The pharmaceutical composition or dietary supplement according to claim 1, in a dosage form for oral administration.

4. The pharmaceutical composition or dietary supplement according to claim 3, in the form of a tablet.

5. The pharmaceutical composition or dietary supplement according to claim 1, wherein the neuropathy is selected from the group consisting of peripheral neuropathy, inflammatory post-traumatic neuropathy, lumbosciatic syndrome, metabolic diabetic neuropathy, mechanical neuropathy due to nerve entrapment and compression, carpal tunnel syndrome, chemotherapy-induced neuropathy, antiretroviral-induced neuropathy, zoster virus neuropathy, and brachial nerve neuropathy due to vaccination.

6. The pharmaceutical composition or dietary supplement according to claim 1, further comprising one or more vitamins selected from the group consisting of vitamin C, vitamin E, vitamin B1, vitamin B2, vitamin B6 and vitamin B12.

7. The composition according claim 1, further comprising pharmaceutically acceptable excipients and/or binders and/or carriers.

* * * * *